US012678023B2

(12) United States Patent
Hauger et al.

(10) Patent No.: US 12,678,023 B2
(45) Date of Patent: Jul. 14, 2026

(54) MEDICAL OPTICAL SYSTEM, DATA PROCESSING SYSTEM, COMPUTER PROGRAM, AND NON-VOLATILE COMPUTER-READABLE STORAGE MEDIUM

(71) Applicant: Carl Zeiss Meditec AG, Jena (DE)

(72) Inventors: Christoph Hauger, Aalen (DE); Stefan Saur, Aalen (DE); Gerald Panitz, Bopfingen (DE)

(73) Assignee: Carl Zeiss Meditec AG, Jena (DE)

( * ) Notice: Subject to any disclaimer, the term of this patent is extended or adjusted under 35 U.S.C. 154(b) by 32 days.

(21) Appl. No.: 17/996,692

(22) PCT Filed: Apr. 22, 2021

(86) PCT No.: PCT/EP2021/060482
§ 371 (c)(1),
(2) Date: Oct. 20, 2022

(87) PCT Pub. No.: WO2021/219473
PCT Pub. Date: Nov. 4, 2021

(65) Prior Publication Data
US 2023/0218142 A1 Jul. 13, 2023

(30) Foreign Application Priority Data

Apr. 27, 2020 (DE) .......................... 102020111376.5

(51) Int. Cl.
*A61B 1/00* (2006.01)
*A61B 1/04* (2006.01)
(Continued)

(52) U.S. Cl.
CPC .. *A61B 1/000094* (2022.02); *A61B 1/000096* (2022.02); *A61B 1/043* (2013.01);
(Continued)

(58) Field of Classification Search
None
See application file for complete search history.

(56) References Cited

U.S. PATENT DOCUMENTS 5,735,276 A * 4/1998 Lemelson .............. A61B 18/20
600/407
6,109,270 A * 8/2000 Mah ....................... A61B 90/10
128/924
(Continued)

FOREIGN PATENT DOCUMENTS

CN 102639049 A 8/2012
CN 106068092 A 11/2016
(Continued)

OTHER PUBLICATIONS

Unger et al., "Artificial neural network approaches for fluorescence lifetime imaging techniques," (May 2, 2016), Optics Letters, vol. 41, No. 11. (Year: 2016).*
(Continued)

*Primary Examiner* — Keith M Raymond
*Assistant Examiner* — Ashish S. Jasani
(74) *Attorney, Agent, or Firm* — Honigman LLP; Brett A. Krueger

(57) ABSTRACT

The invention relates to a medical optical system. The medical optical system comprises: —a microendoscope (3) for capturing histological images, each of which displays a microscopic tissue section (16) of a macroscopic tissue region (15) with a tumor (23); and—a classification device (31) for classifying the macroscopic tissue sections (16) displayed in the histological images as at least one respective tissue section that represents the tumor (23) or a tissue section that represents healthy tissue and for outputting a classification result for each classified microscopic tissue section (16). The medical optical system additionally comprises a combination device (37) which generates a macro- (Continued)

scopic classification image (43) by combining the classification results, said classification image representing the location of the tumor (23) in the macroscopic tissue region (15).

18 Claims, 5 Drawing Sheets

(51) Int. Cl.

| | |
|---|---|
| *A61B 1/06* | (2006.01) |
| *G16H 10/40* | (2018.01) |
| *G16H 30/20* | (2018.01) |
| *G16H 50/20* | (2018.01) |

(52) U.S. Cl.
CPC ........... *A61B 1/0653* (2013.01); *G16H 10/40* (2018.01); *G16H 30/20* (2018.01); *G16H 50/20* (2018.01)

(56) References Cited

U.S. PATENT DOCUMENTS

| | | | | |
|---|---|---|---|---|
| 6,831,781 | B2 | 12/2004 | Tearney et al. | |
| 7,109,505 | B1 | 9/2006 | Sliski et al. | |
| 7,162,292 | B2 | 1/2007 | Ohno et al. | |
| 7,194,118 | B1 | 3/2007 | Harris et al. | |
| 9,754,371 | B2 | 9/2017 | Kateb et al. | |
| 9,921,406 | B2 | 3/2018 | Wang et al. | |
| 2002/0173783 | A1 | 11/2002 | Ohno et al. | |
| 2010/0157308 | A1 | 6/2010 | Xie | |
| 2012/0101374 | A1* | 4/2012 | Tearney ............... | A61B 5/6852 |
| | | | | 600/425 |
| 2013/0178748 | A1 | 7/2013 | Douplik et al. | |
| 2015/0250387 | A1 | 9/2015 | Hauger et al. | |
| 2016/0035093 | A1 | 2/2016 | Kaleb et al. | |
| 2016/0051131 | A1 | 2/2016 | Jeong et al. | |
| 2016/0063724 | A1 | 3/2016 | Tunstall et al. | |
| 2018/0096191 | A1* | 4/2018 | Wan ..................... | G06V 10/772 |
| 2018/0114087 | A1* | 4/2018 | Kamen ................. | G06T 7/0012 |
| 2018/0338802 | A1 | 11/2018 | Wade | |
| 2021/0001154 | A1* | 1/2021 | Dai ....................... | A61N 5/1015 |
| 2023/0030424 | A1* | 2/2023 | Ozcan ............... | G06F 18/24137 |

FOREIGN PATENT DOCUMENTS

| | | | |
|---|---|---|---|
| CN | 107624192 | A | 1/2018 |
| CN | 107667380 | A | 2/2018 |
| CN | 110192141 | A | 8/2019 |
| DE | 102008030590 | A1 | 1/2009 |
| DE | 102014103044 | A1 | 9/2015 |
| DE | 102015200630 | A1 | 7/2016 |
| DE | 102018120750 | B3 | 10/2019 |
| EP | 2335778 | A1 | 6/2011 |
| JP | H09281405 | A | 10/1997 |
| JP | H10333056 | A | 12/1998 |
| JP | 2004000505 | A | 1/2004 |
| JP | 2004024656 | A | 1/2004 |
| WO | 0158346 | A1 | 8/2001 |
| WO | 2008076910 | A1 | 6/2008 |
| WO | 2018152248 | A1 | 8/2018 |

OTHER PUBLICATIONS

Y. Sun et al. "Fluorescence lifetime imaging microscopy for brain tumor image-guided surgery" in Journal of Biomedical Optics 15(5), Sep./Oct. 2010.

Ayachen et al, "Processing and Mosaicing of Fibered Confocal Images", Medical Image Computing and Computer-Assisted Intervention—MICCAI 2006 : 9th International Conference, Copenhagen, Denmark, Oct. 1-6, 2006, Berlin [U.A.] : Springer, DE, (Oct. 1, 2006), pp. 1-5, XP002591322 [Y] 1-4,12-14 * Abschnitt V * [A] 5-11.

International Search Report and Written Opinion for PCT Application PCT/EP2021/060482 dated Apr. 22, 2021.

German Office Action for application No. 102020111376.5.

Japanese Patent Office, Office Action for Application 2022-562839 dated Oct. 24, 2023.

Chinese Office Action for the related Application No. 202180029269.0 dated Jun. 13, 2025.

Chinese Office Action for the related application No. 2021800292690 dated Apr. 20, 2026.

* cited by examiner

15

45

44 44 44

15

43, 45

15

47

117

117 117 117 23

MEDICAL OPTICAL SYSTEM, DATA PROCESSING SYSTEM, COMPUTER PROGRAM, AND NON-VOLATILE COMPUTER-READABLE STORAGE MEDIUM

TECHNICAL FIELD

The present disclosure relates to a medical optical system used to classify the tissue. Additionally, the disclosure relates to a data processing system, a computer program and a non-volatile computer-readable storage medium.

BACKGROUND

Within the scope of treating tumors, attempts are made to act on the tumor in a targeted manner, in order to remove the latter and at the same time largely spare the tissue surrounding the tumor. However, this requires that the position of the tumor in a tissue region is known to the best possible extent in order to be able to in fact restrict the treatment, for instance a resection or irradiation, to the tumor. Moreover, knowledge about the type of tumor present is generally important for the treatment, and so knowledge about the type of tumor is also important in addition to knowledge about the position of the tumor in the tissue region.

By now, systems based on artificial intelligence are also used to distinguish between tumor tissue and healthy tissue, said systems being able to carry out a classification of the imaged tissue into tumor tissue and healthy tissue and detect tumor boundaries on the basis of optical information contained in images.

SUMMARY

The present disclosure provides a medical optical system that allows the determination of the position of a tumor in a tissue region and the provision of information about the position for further use. The present disclosure also provides a data processing system which can be used to determine the position of a tumor in a tissue region and to provide information about the position for further use. Furthermore, the present disclosure provides a computer program and a non-volatile computer-readable storage medium, which facilitate the determination of the position of a tumor in a tissue region and the provision of information about the position for further use.

According to a first aspect of the present disclosure, a medical optical system is made available, the latter comprising an endomicroscope for recording histological images which each represent a microscopic tissue section of a macroscopic tissue region with a tumor. The histological images typically in each case show a tissue section of the tissue area with an edge length of less than 1.0 mm×1.0 mm, typically 0.5 mm×0.5 mm or less. The spatial resolution with which a tissue section is imaged in a histological image is 20 $\mu$m or better, for example 10 $\mu$m, 5 $\mu$m, 3 $\mu$m, 1 $\mu$m or better. In terms of frame rates, rates ranging from approximately 0.5 Hz to approximately 100 Hz can be realized with the endomicroscope, with at least the resolution of 20 $\mu$m being able to be maintained.

Furthermore, the medical optical system according to the disclosure comprises a classification device for classifying the microscopic tissue sections represented in the histological images, as a tissue region representing the tumor or a tissue region representing healthy tissue in each case, and for outputting a classification result for each classified microscopic tissue section. Classification can be implemented with the aid of an artificial intelligence, which may be based on a trained neural network in particular. In this case, training can be implemented by means of training data which contain a number of histological images together with information assigned to the histological images, said information assigning each histological image to a class exhibiting tumor tissue and a class exhibiting healthy tissue. In particular, the classification device may also be configured to classify a microscopic tissue section into a number of classes, of which one class represents healthy tissue and the remaining classes represent different types of tumor tissue. The information assigned to the respective histological images then divides the images contained in the training data into classes of images, one of which represents healthy tissue and the others represent different types of tumor tissue.

The acquisition of histological images for a plurality of microscopic tissue sections of the macroscopic tissue region can be implemented manually or automatically. In the case of a manual acquisition of the histological images, the treating physician chooses the sites at which the histological images are recorded. The coordinates of those sites of the macroscopic tissue region at which the physician records the histological images can be registered with the aid of a navigation system in this case. This allows a subsequent assignment of the images to the microscopic tissue sections for which these were recorded.

If the histological images are acquired automatically, the medical optical system may comprise a scanning device for scanning the macroscopic tissue region with the endomicroscope. In particular, the scanning device may follow a defined path during the scanning procedure. This scanning device should not be mistaken for the scanning device of an endomicroscope which serves to record the histological images by means of a scanning imaging method. While the scanning device of the endomicroscope typically scans an optical fiber over an area of 1.0 mm×1.0 mm, in particular over an area of 0.5 mm×0.5 mm or less, the scanning device for scanning the macroscopic tissue region displaces the distal end of the endomicroscope by an absolute value that typically corresponds to at least the edge length of the images recorded using the endomicroscope. Navigation data from a navigation system may serve to position the endomicroscope by way of the scanning device, the navigation data specifying the positions of the scanning path in relation to the macroscopic tissue region and the homing in on the individual positions of the scanning path being able to be implemented with the aid of said navigation data.

Finally, the medical optical system according to the disclosure comprises a combination device which generates a macroscopic classification image by combining the classification results, the classification image representing the position of the tumor in the macroscopic tissue region. In particular, the combination device may also be configured to derive the macroscopic profile of a tumor on the basis of the classification results. With the aid of the medical optical system according to the disclosure, it is thus possible to derive the position, the extent and the macroscopic profile of a tumor, in particular the profile of the boundary between tumor tissue and healthy tissue, on the basis of histological images obtained at discrete points. The assignment of the classification results to their position in the macroscopic tissue region can be implemented by means of the navigation data registered or used when positioning the endomicroscope.

This classification image can then be used further in a wide variety of different ways. By way of example, the classification image can be overlaid on an overview image of the macroscopic tissue region in order to emphasize the tumor in the overview image and in order to represent the boundary between tumor tissue and healthy tissue in the overview image. Then, in the superposition, the area taken up by the image regions representing the individual classification results in the classification image represents the area of the tumor and the edge of the area taken up by the image regions representing the individual classification results in the classification image represents the boundary of the tumor.

Moreover, it is possible to position a treatment system for treating the tumor tissue on the basis of the position of the tumor shown in the classification image. The medical optical system according to the disclosure therefore facilitates the precise detection of the position of a tumor in a tissue region, for example immediately before a treatment, for instance a resection of tumor tissue or an irradiation of tumor tissue. It is then no longer necessary for the position of the tumor tissue in the tissue region to be determined exactly in advance. Moreover, there is the option of verifying positions of the tumor as determined presurgery and optionally of even finding tumor regions which were not found presurgery.

In particular, the classification device can be configured to carry out the classification on the basis of at least one of the following alternatives:

the morphology of the microscopic tissue section represented in the respective histological image;

the intensity of the fluorescence radiation emitted by the microscopic tissue section represented in the respective histological image;

the decay behavior of the fluorescence radiation emitted by the microscopic tissue section represented in the respective histological image;

the spectral reflection properties of the microscopic tissue section represented in the respective histological image.

All these alternatives can be realized on the basis of the histological images and are suitable for distinguishing between tumor tissue and healthy tissue. It is particularly advantageous if two or more of these alternatives are used in combination with one another for classification purposes. Depending on the alternative, the neural network then is trained accordingly. By way of example, if this should be a classification on the basis of the morphology, the images used in the training data may be, e.g., simple grayscale images, from which the neural network can learn the morphological forms typical for the identification of tumor tissue. Should the classification be implemented on the basis of the intensity of fluorescence radiation, the training data may contain images, some of which show the intensity of fluorescence radiation of tumor tissue and the rest show the intensity of fluorescence radiation in healthy tissue. In the case of a classification on the basis of the decay behavior of fluorescence radiation, the training data in each case contain a sequence of images covering a certain period of time, from which time profiles of the fluorescence radiation characteristic for tumor tissue and healthy tissue can be learnt. In the case of a classification on the basis of the spectral reflection properties of the imaged tissue, the training data sets may comprise images with the highest possible spectral resolution such that the neural network learns to distinguish tumor tissue from healthy tissue on the basis of the spectral signature. The images in each case are assigned information which assigns these to a class representing tumor tissue or a class representing healthy tissue. If the classification device of the medical optical system is configured to classify a microscopic tissue section into a number of classes, of which one class represents healthy tissue and the remaining classes represent different types of tumor tissue, it may be advantageous, in order to improve the identification of the individual types of tumors, to use two or more of the aforementioned alternatives for classifying the microscopic tissue section represented in the respective histological images.

The medical optical system may comprise optical observation equipment, for example a surgical microscope for producing an overview image of the macroscopic tissue region, and an overlay apparatus, the overlay apparatus being configured to overlay the classification image on the overview image. A registration unit is advantageously present in order to facilitate a positionally accurate superposition, the registration unit registering the classification image and the overview image to one another, with it being possible, for example, to align certain features that are identifiable in both images. In particular, work may also be carried out here with markers that are present both in the overview image and in the classification image and that are aligned to one another for registration purposes. Moreover, there is the option of using a navigation system which acquires both the position and orientation of the optical observation equipment relative to the tissue region and the position and the orientation of the endomicroscope when recording the histological images in a common coordinate system and which allows alignment of the classification image and the overview image on the basis of the registered positions. With the aid of the classification image being overlaid, it is possible to mark the site to be treated for the benefit of a treating surgeon so that they can exclusively treat tumor regions in a targeted manner.

The presence of optical observation equipment moreover allows also the use of data from images obtained by the optical observation equipment for classification purposes. By way of example, images obtained by the optical observation equipment can be used to determine the intensity of fluorescence radiation or the decay behavior of fluorescence radiation at the site at which a histological image is recorded and to undertake the classification on the basis of the determined fluorescence intensity or the determined decay behavior in combination with morphological information obtained on the basis of the histological image.

If the medical optical system, in addition or as an alternative to the optical observation equipment, comprises a treatment system for the local treatment of tissue and a positioning device for positioning the treatment system such that a determined site of the tissue region is treated, the positioning device is designed to undertake the positioning on the basis of the classification image in a development of the disclosure. By way of example, the treatment system may comprise an irradiation system for the targeted irradiation of a certain site with therapeutic radiation. In this case, the positioning device is designed to align the irradiation system with the determined site of the tissue region on the basis of the classification image for the purposes of positioning said irradiation system. Alternatively, the treatment system may comprise an applicator for the local application of therapeutic radiation at or in the determined site. In an advantageous development of the disclosure, the positioning device then is designed to guide the applicator to the determined site by means of a robot, the guidance being implemented on the basis of the classification image. In this way, there can be highly precise local irradiation of the tumor with therapeutic radiation. However, naturally, the treatment system can also find use for robot-guided resection of tumor tissue.

Moreover, a data processing system is made available according to the disclosure, said data processing system comprising:

a receiving interface for receiving a plurality of histological images, which each represent a different microscopic tissue section of a macroscopic tissue region with a tumor;

a classification device for classifying the microscopic tissue sections represented in the histological images, as a tissue region representing the tumor or a tissue region representing healthy tissue in each case, and for outputting a classification result for each classified microscopic tissue section;

and a combination device which generates a macroscopic classification image by combining the classification results, the classification image representing the position of the tumor in the macroscopic tissue region.

The data processing system according to the disclosure renders it possible the creation of a classification image on the basis of images obtained using an endomicroscope. Therefore, together with an endomicroscope, the data processing system can form a medical optical system according to the disclosure, as described above. In this case, the classification device of the data processing system can also use images of optical observation equipment for classification purposes, said images then being received via a receiving interface. Otherwise, statements made in relation to the classification device of the medical optical system according to the disclosure apply to the classification device of the data processing system.

Moreover, a computer program is also made available according to the disclosure. The computer program comprises instructions which, when executed on a computer, prompt the latter:

to receive a plurality of histological images, which each represent a different microscopic tissue section of a macroscopic tissue region with a tumor;

to classify the microscopic tissue sections represented in the histological images, as a tissue region representing the tumor or a tissue region representing healthy tissue in each case, and to output a classification result for each classified microscopic tissue section;

and to generate a macroscopic classification image by combining the classification results, the classification image representing the position of the tumor in the macroscopic tissue region.

The computer program according to the disclosure renders it possible to configure a commercially available computer as a data processing system according to the disclosure. Developments of the computer program according to the disclosure arise from the developments of the medical optical system according to the disclosure.

According to the disclosure, a non-volatile computer-readable storage medium is also made available. The non-volatile computer-readable storage medium contains instructions stored thereon which, when executed on a computer, prompt the computer to receive a plurality of histological images, which each represent a different microscopic tissue section of a macroscopic tissue region with a tumor;

to classify the microscopic tissue sections represented in the histological images, as a tissue section representing the tumor or a tissue section representing healthy tissue in each case, and to output a classification result for each classified microscopic tissue section;

and to generate a macroscopic classification image by combining the classification results, the classification image representing the position of the tumor in the macroscopic tissue region.

The non-volatile computer-readable storage medium allows the computer program according to the disclosure to be loaded onto a commercially available computer and hence configure the latter as data processing system according to the disclosure. Advantageous developments of the non-volatile computer-readable storage medium according to the disclosure emerge from the advantageous configurations of the medical optical system according to the disclosure.

Moreover, a medical therapeutic system is made available according to a further aspect of the present disclosure. Said medical therapeutic system comprises at least one item of medical image recording equipment for recording an image of a tissue region with a tumor. In particular, the medical image recording equipment can be a camera integrated in a surgical microscope. However, it may also be a camera that is purely present for the purposes of recording images and not integrated in a surgical microscope. Furthermore, the medical image recording equipment can be a camera integrated into an endoscope. The medical therapeutic system moreover comprises a classification device for classifying tissue sections of the tissue region represented in image sections of the recorded image, as a tissue section representing the tumor or as a tissue section representing healthy tissue in each case, and for outputting a classification result for each classified tissue section. The medical therapeutic system also comprises a treatment system for the local treatment of tissue and a positioning device for positioning the treatment system such that only tissue sections that have been classified as tissue sections representing the tumor are treated. In this case, the classification device can be designed like the classification device of the medical optical system according to the disclosure, with this classification device classifying tissue sections of an image obtained by the medical image recording equipment instead of the microscopic tissue sections represented in the histological images. The training data for training the classification device then contain images that correspond to the images recorded by the medical image recording equipment.

The medical therapeutic system according to the disclosure allows the treatment to be carried out immediately following the classification. Particularly when the treatment system and the medical image recording equipment form a unit, there is no need for a coordinate transformation to be carried out in the process, as would be required, for example, if the classification data would have been obtained presurgery. By way of example, a treatment system and an item of medical image recording equipment can both be integrated in a surgical microscope or an endoscope. In this case, there is the option of the surgical microscope or the endoscope being provided with a focusable illumination apparatus which allows the focusing of therapeutic radiation on a determined tissue section. However, there is also the option of providing a robot-guided applicator as a treatment system, by means of which a radiation source can be guided to or into the tissue section to be treated. Targeted local irradiation of the tumor is possible in this way.

Further features, properties and advantages of the present disclosure will become apparent from the following description of exemplary embodiments with reference to the accompanying figures.

DETAILED DESCRIPTION

For explanatory purposes, the disclosure will be described in detail below on the basis of exemplary embodiments. In this case, FIG. 1 shows an exemplary embodiment of a medical optical system comprising an item of optical observation equipment in the form of a surgical microscope 1, an endomicroscope 3 and a computer 5 as data processing system.

Figure 1:
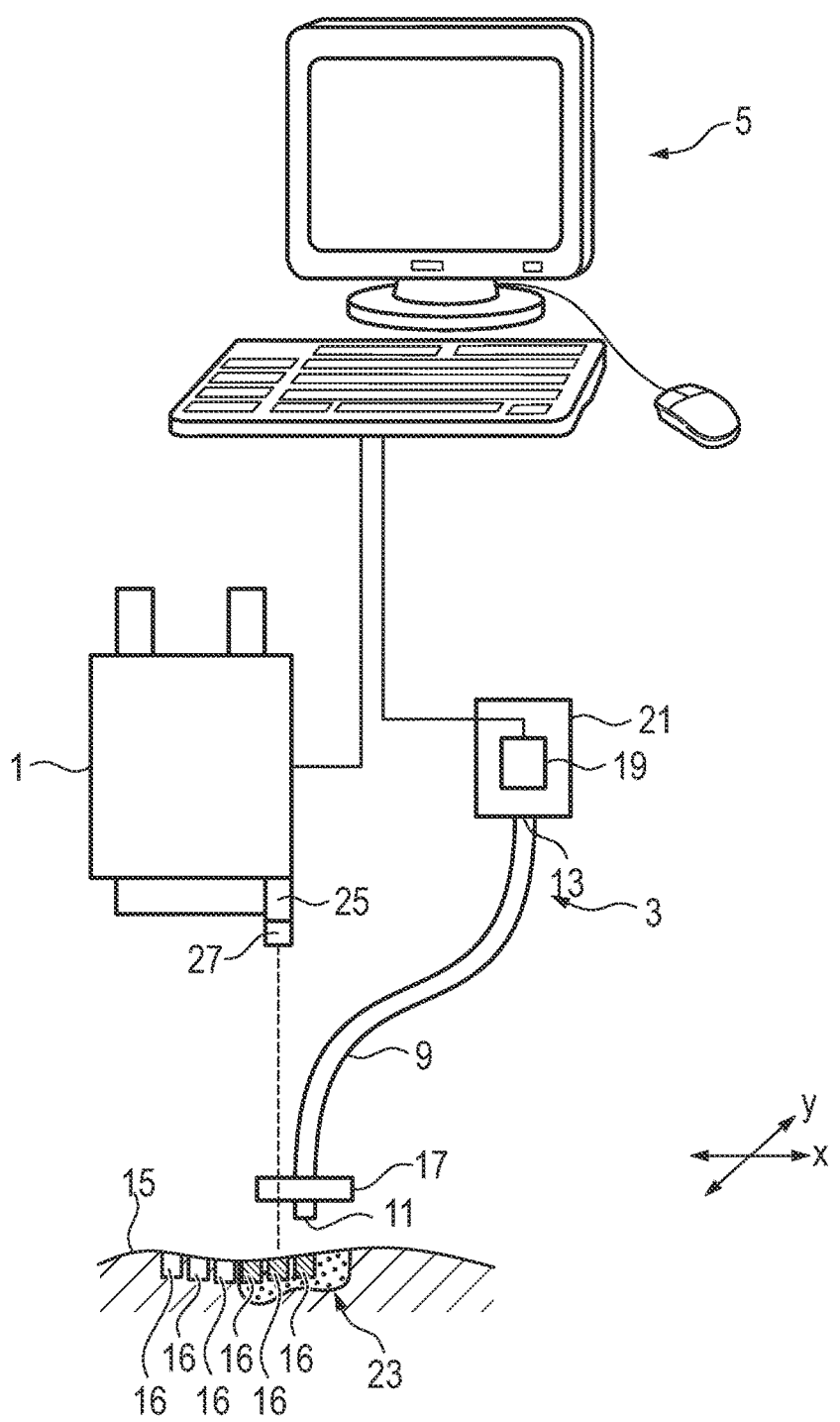
FIG. 1 shows a medical optical system having an endomicroscope, a surgical microscope and an irradiation system.

The endomicroscope 3 shown in FIG. 1 comprises a rigid or flexible tube 9 with a first end 11 and a second end 13. The first end 11 faces the observation object, which is a macroscopic tissue region 15 with a tumor 23 in the present exemplary embodiment, and is located in a scanning device 17, with the aid of which the first end 11 of the tube 9 can be moved along two lateral directions, referred to as x-direction and y-direction below, with respect to the observation object 15. By way of example, the scanning device 17 can be realized by means of piezo-actuators.

An optical fiber (not depicted in the figure) is arranged in the interior of the tube 9 and can be used in the present exemplary embodiment to pass over a microscopic tissue section 16 of the macroscopic tissue region 15 of 0.5 mm×0.5 mm in raster-type fashion in order to record a histological image of the microscopic tissue section 16. In the present exemplary embodiment, scanning is implemented by means of a microelectromechanical system (MEMS). By way of example scanning by means of a microelectromechanical system is described in US 2016/0051131 A1. Reference is made to this document in respect of the scanning for obtaining the histological image. After a histological image was recorded, the first end 11 of the tube 9 is offset by a certain increment to a new microscopic tissue section 16 by means of the scanning device 17, said new microscopic tissue section then being passed over by the optical fiber in raster-type fashion in order to record a further histological image. The increment is 0.5 mm in the present exemplary embodiment, and so the microscopic tissue section 16 by which the histological image is recorded adjoins that microscopic image section 16 to which the previously recorded histological image was recorded. However, the increment may also be greater than or less than the lateral extent of the microscopic tissue sections 16; that is to say greater than or less than 0.5 mm in the present exemplary embodiment. An increment less than the lateral extent of the microscopic tissue sections 16 leads to an overlap of the microscopic tissue sections 16 imaged in the histological images, which may be advantageous if these should be combined in mosaic-like fashion to form a larger image since the histological images can then be aligned relative to one another on the basis of the overlapping regions. By contrast, an increment greater than the lateral extent of the microscopic tissue sections 16 offers the advantage that relatively large tissue regions can be scanned quickly. In order to be able to combine the histological images to form a relatively large image in this case, the position of the microscopic tissue sections recorded in each case can be registered, for example with the aid of a navigation system, and the combination can be implemented on the basis of the registered positions. However, if the increment is greater than the lateral extent of the microscopic tissue sections 16, it should not be greater than the scale at which changes in the tissue may occur in order to be able to sufficiently accurately determine the point at which a change occurs. There is also the option of the increments being different in different sections of the macroscopic tissue region 15, for example if a physician would like to classify one or more sections more closely than others.

It should be observed here that the scanning device 17 present in the current exemplary embodiment is purely optional. There also is the option of a treating physician manually positioning the endomicroscope 3 for the purposes of recording the histological images. In this case, the positions at which the physician records histological images can be registered by means of a navigation system and can be stored for later use.

The second end 13 of the pipe 9 faces a sensor 19, by means of which it is possible to capture luminous energy transferred by the optical fiber. The sensor 19 is located in a housing 21, which is designed as a separate module in the present exemplary embodiment but which can also be designed as a handle, and in which, moreover, a light source (not illustrated in the figure) for generating illumination light for illuminating the macroscopic tissue region 15 and an input coupling apparatus for coupling the illumination light into the optical fiber are housed. In particular, the light source can be a laser light source. However, the light source can also be arranged outside of the housing 21 and be connected to the latter by way of a light guide. Then, the output end of the light guide is situated in the housing 21. In this case, the input coupling apparatus input couples the illumination light of the optical fiber emerging from the output end of the light guide. The illumination light can be white light, i.e., have a broadband spectrum, or light with a spectrum that consists of one or more narrowband spectral ranges, in particular spectral lines, for example of one or more narrowband spectral ranges or spectral lines suitable for exciting a fluorescence of a fluorescent dye situated in the macroscopic tissue region 15. By way of example, the fluorescent metabolite protoporphyrin IX (PpIX) is a suitable fluorescent dye.

Illumination light input coupled into the optical fiber is transmitted through the optical fiber to the first end 11 of the tube, where it emerges from the optical fiber in the direction of the macroscopic tissue region 15. Illumination light reflected by the macroscopic tissue region 15 or light excited by the illumination light and emitted by the macroscopic tissue region 15, for instance fluorescent light, enters into the optical fiber in turn and is guided by the latter to the second end 13 of the tube 9, where it emerges in the direction of the sensor 19. Moreover, focusing optical units can be located at, or in front of, the ends of the optical fiber and these can be used to focus light onto the surface of the macroscopic tissue region 15 or onto the sensor 19.

In particular, the endomicroscope 3 can be embodied as a confocal endomicroscope. In addition or as an alternative thereto, it can also be embodied as an endomicroscope for carrying out optical coherence tomography (OCT). Confocal microscopy and optical coherence tomography are well-known methods and are described in US 2010/0157308 A1 and U.S. Pat. No. 9,921,406 B2, for example. Therefore, the description of details in respect of confocal microscopy and in respect of optical coherence tomography is dispensed with in the scope of the present description. Instead, reference is made to US 2010/0157308 A1 and U.S. Pat. No. 9,921,406 B2.

Recording a histological image with the aid of the endomicroscope 1 is controlled with the aid of the computer 5 in the present exemplary embodiment. However, the control can also be implemented by means of a dedicated control device. The computer 5 used for controlling in the present exemplary embodiment is connected both to the microelectromechanical system used for the scanning and to the sensor 19. In the present exemplary embodiment, the microelectromechanical system is controlled by the computer 5 in such a way that the microscopic tissue section 16 is scanned at a multiplicity of grid points. At each grid point there is an illumination of the grid point with illumination light and a recording of the illumination light reflected by the grid point or of the light emitted by the grid point on account of an excitation by means of the illumination light. Then, the computer generates an image from the illumination light reflected by the grid points or from the light emitted by the grid points, the pixel grid of said image corresponding to the grid used during the scanning. The resolution of the image produced thus is typically 20 μm or better, preferably 10 μm or better, for example 5 μm, 3 μm, 1 μm, 0.7 μm, or even better. In this case, the histological image typically shows a tissue section of 1 mm² or less, for example 0.5 mm², 0.2 mm², 0.1 mm² or even less. In the present exemplary embodiment, the optical fiber, the microelectromechanical system, the sensor 19, and the computer 5 together form a recording apparatus for recording histological images, that is to say for recording images that facilitate the determination of histological information items such as, for instance, the tumor cell proportion of the tissue depicted in the image or the oxygen content, the pH value, the concentration of $H_2O_2$ or other oxygen derivatives, etc., of the tissue depicted in the image, etc. By way of example, tumor cells can then be identified in the histological image on the basis of morphological criteria, for instance the cell structure, the size of the cell nucleus, etc., optionally with the aid of staining means for increasing the contrast.

Figure 2:
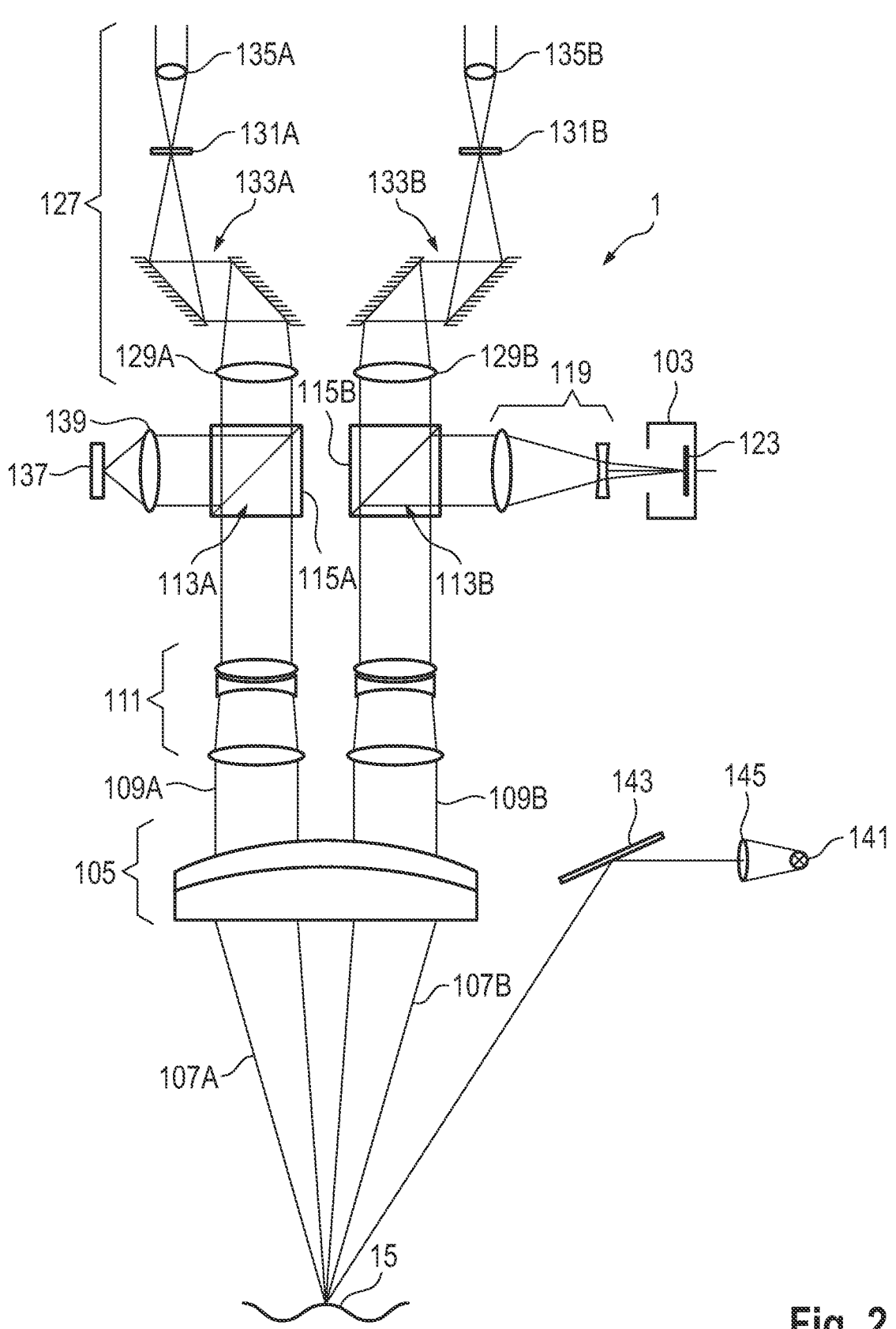
FIG. 2 shows the structure of a surgical microscope in a schematic representation.
Figure 3:
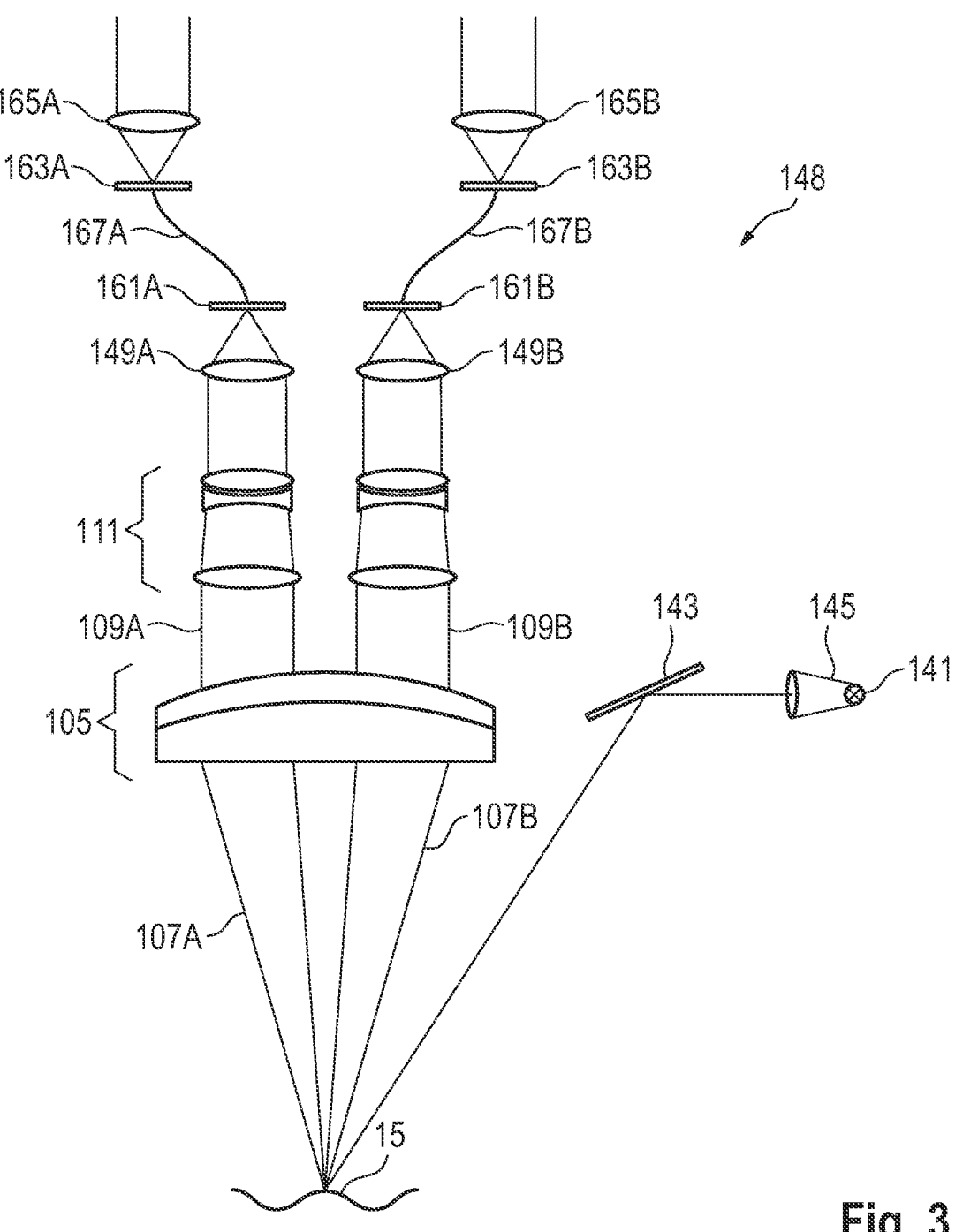
FIG. 3 shows an alternative configuration of the surgical microscope.

FIG. 2 shows a schematic illustration of a possible structure of the surgical microscope 1, as can find use in the medical optical system of FIG. 1. FIG. 3 shows a possible alternative structure.

The surgical microscope 1 shown in FIG. 2 comprises, as essential components, an objective 105 that is to face an observation object, that is to say the macroscopic tissue region 15 with a tumor 23 in the present exemplary embodiment, which objective can be embodied in particular as an achromatic or apochromatic objective. In the present exemplary embodiment, the objective 105 consists of two partial lenses that are cemented to one another and form an achromatic objective. The observation object 15 is arranged in the focal plane of the objective 105 such that it is imaged at infinity by the objective 105. Expressed differently, a divergent beam 107A, 107B emanating from the observation object 15 is converted into a parallel beam 109A, 109B during its passage through the objective 105.

A magnification changer 111 is arranged on the observer side of the objective 105, which magnification changer can be embodied either as a zoom system for changing the magnification factor in a continuously variable manner as in the illustrated exemplary embodiment, or as what is known as a Galilean changer for changing the magnification factor in a stepwise manner. In a zoom system, constructed by way of example from a lens combination having three lenses, the two object-side lenses can be displaced in order to vary the magnification factor. In actual fact, however, the zoom system also can have more than three lenses, for example four or more lenses, in which case the outer lenses then can also be arranged in a fixed manner. In a Galilean changer, by contrast, there are a plurality of fixed lens combinations which represent different magnification factors and which can be introduced into the beam path alternately. Both a zoom system and a Galilean changer convert an object-side parallel beam into an observer-side parallel beam having a different beam diameter. In the present exemplary embodiment, the magnification changer 111 is already part of the binocular beam path of the surgical microscope 1, i.e., it has a dedicated lens combination for each stereoscopic partial beam path 109A, 109B of the surgical microscope 1. In the present exemplary embodiment, a magnification factor is adjusted by means of the magnification changer 111 by way of a motor-driven actuator which, together with the magnification changer 111, is part of a magnification changing unit for adjusting the magnification factor.

The magnification changer 111 is followed on the observer side by an optical interface arrangement 113A, 113B, by means of which external equipment can be connected to the surgical microscope 1 and which comprises beam splitter prisms 115A, 115B in the present exemplary embodiment. However, in principle, use can also be made of other types of beam splitters, for example partly transmissive mirrors. In the present exemplary embodiment, the optical interfaces 113A, 113B serve to output couple a beam from the beam path of the surgical microscope 1 (beam splitter prism 115B) and to input couple a beam into the beam path of the surgical microscope 1 (beam splitter prism 115A).

In the present exemplary embodiment, the beam splitter prism 115A in the partial beam path 109A serves to mirror information or data for an observer into the partial beam path 109A of the surgical microscope 1 with the aid of a display 137, for example a digital mirror device (DMD) or an LCD display, and an associated optical unit 139 by means of the beam splitter prism 115A. By way of example, a colored marking labeling the tumor 23 in the observed macroscopic tissue region 15 can be overlaid on the image obtained by the surgical microscope 1. A camera adapter 119 with a camera 103 secured thereto, said camera being equipped with an electronic image sensor 123, for example with a CCD sensor or a CMOS sensor, is arranged at the optical interface 113B in the other partial beam path 109B. It is possible by means of the camera 103 to record an electronic image and, in particular, a digital image of the observation object 15. The image sensor used can also be, in particular, a multispectral sensor or a hyperspectral sensor comprising not just three spectral channels (e.g., red, green, and blue), but rather a multiplicity of spectral channels.

The optical interface 113 is followed on the observer side by a binocular tube 127. The latter has two tube objectives 129A, 129B, which focus the respective parallel beam 109A, 109B onto an intermediate image plane 131, i.e., image the observation object 15 onto the respective intermediate image plane 131A, 131B. The intermediate images situated in the intermediate image planes 131A, 131B are finally imaged at infinity in turn by eyepiece lenses 135A, 135B, such that an observer can observe the intermediate image with a relaxed eye. Moreover, the distance between the two partial beams 109A, 109B is increased in the binocular tube by means of a mirror system or by means of prisms 133A, 133B in order to adapt said distance to the interocular distance of the observer. In addition, image erection is carried out by the mirror system or the prisms 133A, 133B.

The surgical microscope 1 moreover is equipped with an illumination apparatus, by means of which the observation object 15 can be illuminated with illumination light. To this end, the illumination apparatus in the present exemplary embodiment has a white-light source 141, for example a halogen lamp or a gas discharge lamp. The light emanating from the white-light source 141 is directed in the direction of the observation object 15 via a deflection mirror 143 or a deflection prism in order to illuminate said object. Furthermore, an illumination optical unit 145 is present in the illumination apparatus, said illumination optical unit ensuring uniform illumination of the entire observed observation object 15.

The illumination can be influenced in the surgical microscope 1 illustrated in FIG. 2. By way of example, a filter can be introduced into the illuminating beam path, said filter transmitting only a narrow spectral range from the wide spectrum of the white-light source 141, e.g., a spectral range that enables the excitation of fluorescence of a fluorescent dye situated in the observation object 15. In order to observe the fluorescence, filters 137A, 137B can be introduced into the observation partial beam paths, said filters filtering out the spectral range used to excite the fluorescence in order to be able to observe the fluorescence. To illuminate the observation object 15 only using the spectral range of the illumination light required for exciting the fluorescence, there is the option of using a narrowband light source, for example a laser light source, which substantially only emits in the spectral range required for exciting the fluorescence, rather than using a white-light source in conjunction with a filter. In particular, the illumination apparatus may also comprise a device facilitating an interchange between a white-light source and a narrowband light source.

Attention is drawn to the fact that the illumination beam path illustrated in FIG. 2 is highly schematic and does not necessarily reproduce the actual course of the illumination beam path. In principle, the illumination beam path can be embodied as so-called oblique illumination, which comes closest to the schematic illustration in FIG. 2. In such oblique illumination, the beam path extends at a relatively large angle (6° or more) with respect to the optical axis of the objective 5 and, as illustrated in FIG. 2, may extend completely outside the objective. Alternatively, however, there is also the possibility of allowing the illumination beam path of the oblique illumination to extend through a marginal region of the objective 105. A further possibility for the arrangement of the illumination beam path is what is known as 0° illumination, in which the illumination beam path extends through the objective 105 and is input coupled into the objective 105 between the two partial beam paths 109A, 109B, along the optical axis of the objective 105 in the direction of the observation object 15. Finally, it is also possible to design the illumination beam path as what is known as coaxial illumination, in which a first illumination partial beam path and a second illumination partial beam path are present. The partial beam paths are coupled into the surgical microscope 1 via one or more beam splitters parallel to the optical axes of the observation partial beam paths 109A, 109B, such that the illumination extends coaxially with respect to the two observation partial beam paths.

In the embodiment variant of the surgical microscope 1 shown in FIG. 2, the objective 105 consists only of one achromatic lens. However, use can also be made of an objective lens system composed of a plurality of lenses, in particular what is known as a varioscope objective, by means of which it is possible to vary the working distance of the surgical microscope 1, i.e., the distance between the object-side focal plane and the vertex of the first object-side lens surface of the objective 105, also referred to as front focal distance. The observation object 15 arranged in the focal plane is imaged at infinity by a varioscope objective, too, and so a parallel beam is present on the observer side.

FIG. 3 shows an example of a digital surgical microscope 148 in a schematic representation. In this surgical microscope, the main objective 105, the magnification changer 111, and the illumination system 141, 143, 145 do not differ from the surgical microscope 1 with the optical viewing unit that is illustrated in FIG. 2. The difference lies in the fact that the surgical microscope 148 shown in FIG. 3 does not comprise an optical binocular tube. Instead of the tube objectives 129A, 129B from FIG. 2, the surgical microscope 148 from FIG. 3 comprises focusing lenses 149A, 149B, by means of which the binocular observation beam paths 109A, 109B are imaged on digital image sensors 161A, 161B. Here, the digital image sensors 161A, 161B can be, for example, CCD sensors or CMOS sensors. The images recorded by the image sensors 161A, 161B are transmitted to digital displays 163A, 163B, which may be embodied as LED displays, as LCD displays, or as displays based on organic light-emitting diodes (OLEDs). As in the present example, eyepiece lenses 165A, 165B can be assigned to the displays 163A, 163B, by means of which lenses the images presented on the displays 163A, 163B are imaged at infinity such that a viewer can view said images with relaxed eyes. The displays 163A, 163B and the eyepiece lenses 165A, 165B can be part of a digital binocular tube; however, they can also be part of a head mounted display (HMD) such as, e.g., a pair of smartglasses. Naturally, the images recorded by the image sensors 161A, 161B can also be transferred to a monitor. Suitable shutter glasses can be used for the three-dimensional observation of the image depicted on the monitor.

The medical optical system of the exemplary embodiment shown in FIG. 1 moreover comprises a radiation light source 25 that emits therapeutic radiation, and a positioning device 27. Using the light of the irradiation light source 25 and with the aid of the positioning device 27, it is possible to illuminate a determined site of the macroscopic tissue region 15 with the therapeutic radiation. In this case, the illumination light source 25 can be for example a laser emitting the therapeutic radiation or a conventional light source, which can be focused on a site of the macroscopic tissue region 15 by means of a suitable lens or a suitable lens system. The beam of the therapeutic radiation can be positioned on the macroscopic tissue region 15 by means of the positioning device 27. In the present exemplary embodiment, the positioning device is realized as a galvanometer scanner, with the aid of which the direction of the illumination radiation can be suitably deflected. However, for the purposes of positioning the beam of the therapeutic radiation on the macroscopic tissue region 15, there is also the option of using a tiltable mount of the irradiation light source 25, rather than the galvanometer scanner, and arranging the irradiation light source 25 on a displaceable carriage.

Figure 4:
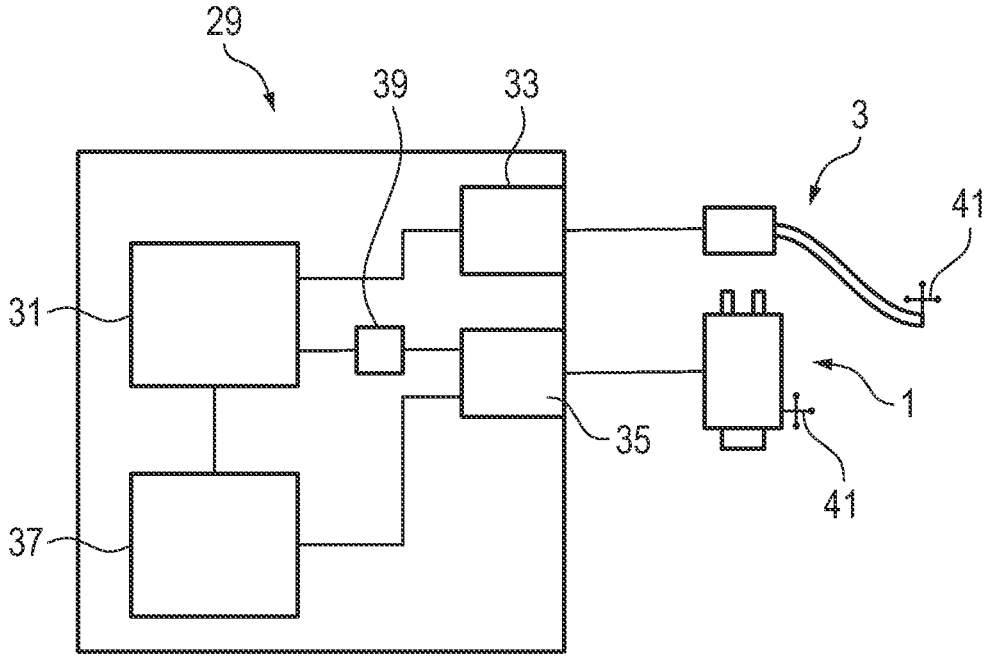
FIG. 4 shows the components of a data processing system as is used in the medical optical system from FIG. 1.

In order to only irradiate those tissue sections of the macroscopic tissue region 15 that actually represent tumor tissue with the therapeutic radiation, the medical optical system comprises a classification device which is used in the present exemplary embodiment to classify microscopic tissue sections 16, of which the endomicroscope 3 has recorded histological images, into one of two classes in each case. In this case, the one class represents the class of tissue representing tumor tissue (the corresponding microscopic tissue sections 16 are hatched in FIG. 1) and the other class represents the class of tissue representing healthy tissue. The classification device is part of a data processing system 19 which is realized by the computer 5 in the present exemplary embodiment. The software components of the data processing system 19 implemented on the computer are depicted schematically in FIG. 4. However, rather than in the computer 5, these software components can also be implemented in the surgical microscope 1, for example, should the latter be equipped with a suitable CPU and a suitable memory. Finally, there is also the option of configuring the data processing system as a dedicated unit.

In addition to the classification device 31, the data processing system 29 comprises a first interface 33, which serves as an input interface for receiving histological images from the endomicroscope 3 in the present exemplary embodiment. Moreover, it comprises a second interface 35 which, in the present exemplary embodiment, serves to exchange data with the surgical microscope 1. However, rather than using two separate interfaces, use can alternatively also be made of a single interface, by means of which data can be exchanged with the surgical microscope 1 and the endomicroscope 3. Examples of such an interface include Bluetooth interfaces, WLAN interfaces or ethernet interfaces. Furthermore, the data processing system 29 comprises a combination device 37 and a selection device 29, the purposes of which are explained below.

As already mentioned, the classification device 31 serves to classify the microscopic tissue sections 16 depicted in histological images. To this end, the classification device 31 receives histological images from the endomicroscope 3 via the first interface 33 in order to classify the microscopic tissue sections 16 of the macroscopic tissue region 15 imaged therein. In the present exemplary embodiment, the classification is implemented at least on the basis of morphological criteria, on the basis of which tumor tissue can be distinguished from healthy tissue. To this end, the classification device 31 of the exemplary embodiment comprises a trained neural network that has been trained with training data comprising a multiplicity of histological images and, for each histological image, an indication as to whether this shows healthy tissue or tumor tissue. How to be able to distinguish tumor tissue from healthy tissue on the basis of morphological criteria has been learned by the neural network on the basis of these training data. Should the classification be implemented on the basis of other criteria rather than on the basis of morphological criteria in alternative exemplary embodiments, the neural network has been trained accordingly using different training data. By way of example, the training data contain histological images showing the fluorescence intensity of microscopic tissue sections 16 if the classification should be implemented on the basis of the fluorescence intensity, images showing the spectral intensity distribution of the light reflected by microscopic tissue sections 16 if the classification should be implemented on the basis of the spectral intensity distribution, or series of histological images covering a certain period of time, each series showing the profile of the fluorescence intensity fora microscopic tissue section 16 over the determined period of time, if the classification should be implemented on the basis of the decay behavior of the fluorescence intensity.

Optionally, there is the option of carrying out the classification not only on the basis of the histological images but additionally on the basis of an image recorded using the surgical microscope 1. In the present exemplary embodiment, in which morphological criteria determined on the basis of the histological images are used for the classification, a fluorescence image recorded using the surgical microscope 1, i.e., an image reproducing the intensity of the fluorescence radiation emitted by the macroscopic tissue region 15, is additionally used for the classification. In this case, the selection device 39 selects those image portions from the fluorescence image received from the surgical microscope 1 which correspond to the microscopic tissue section 16 reproduced in the histological images, and assigns these to the histological images. To facilitate this, use is made in the present exemplary embodiment of a navigation system which detects position and orientation of the distal end 9 of the endomicroscope 3 and of the surgical microscope 1 in a common coordinate system with the aid of suitable digital or physical markers 41. In this way, it is firstly possible to determine the position of the macroscopic tissue region 15 at which the histological image is recorded and the alignment of the surgical microscope 1 in which the fluorescence image was recorded. Using the alignment of the surgical microscope 1 and the distance of the surgical microscope 1 from the macroscopic tissue region 15, which is likewise provided with a marker (not depicted), directly or indirectly (marker at a site connected to the macroscopic tissue region), it is then possible to determine the exact position, in the fluorescence image recorded using the surgical microscope 1, of the microscopic tissue section 16 depicted in the histological image.

In order to be able to determine the classification on the basis of the histological images and the data about the fluorescence intensity obtained from the fluorescence image, the neural network is then trained with training data in which each histological image is assigned a fluorescence intensity detected for the tissue shown in the respective histological image and which for each of these assignments contain information as to whether this shows healthy tissue or tumor tissue.

Even though the fluorescence intensity is optionally additionally used for the classification of the microscopic tissue sections 16 depicted in the histological images in the present exemplary embodiment, other variables that can be derived from the image obtained by the surgical microscope 1 may additionally or alternatively be used. By way of example, the decay behavior of the fluorescence radiation at the locations at which histological images were recorded or are recorded can be determined from an image series recorded by the surgical microscope 1. Should the surgical microscope 1 be equipped with a multispectral sensor, there is the option of using an image recorded by the surgical microscope 1 to use the spectral intensity distribution at the locations of the macroscopic tissue region 15 at which histological images were recorded or are recorded for classification purposes. Depending on which additional data are used for classification purpose in addition to the histological images, the training data sets for the neural network contain appropriate information.

In further embodiment variants, there also is the option of recording fluorescence images as histological images themselves and, in that case, to carry out the classification on the basis of the fluorescence intensity of the microscopic tissue section 16 imaged in the respective histological image or on the basis of the decay behavior of the fluorescence intensity of the microscopic tissue section 16. In the latter case, a series of histological images representing a certain period of time is recorded for each microscopic tissue section 16 of the macroscopic tissue region 15, the decay behavior of the fluorescence radiation being able to be determined from said series. Naturally, training data comprising fluorescence images or series of fluorescence images are used to train the neural network in this case.

Especially if it is not only one criterion that is used for classifying the microscopic tissue sections 16 imaged in the histological images, there additionally is the option of carrying out not only a classification into two classes but a classification into a plurality of classes, with one class representing healthy tissue and the remaining classes representing different types of tumor tissue. In this case, the training data used to train the neural network do not only contain the histological images or optionally the combinations of histological images with fluorescence intensities, decay times, spectral intensity distributions, etc., but also information assigned to the images or combinations, said information not only specifying whether the respective image or the respective combination represents healthy tissue or tumor tissue but also, if an image or a combination represents tumor tissue, the type of tumor tissue.

Figure 5:
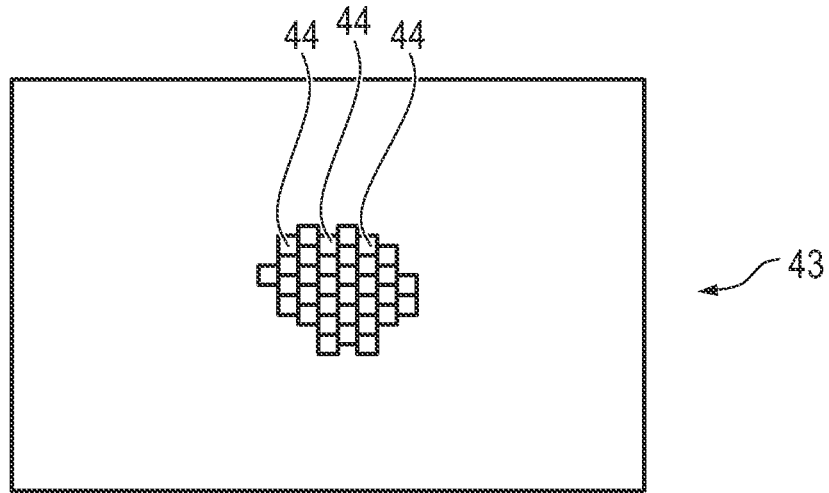
FIG. 5 shows a classification image.

The medical optical system according to the disclosure is used to scan the macroscopic tissue region 15 using the endomicroscope 3, with a histological image of the respective microscopic tissue section 16 being recorded at each scanning point. Then, each histological image is transmitted via the interface 33 to the classification device 31 which carries out the classification on the basis of the trained criteria, optionally using criteria obtained from an image recorded by the surgical microscope 1, and outputs a classification result to the combination device 37 for each histological image. The combination device 37 is a computer routine which produces a classification image 43 from the classification results, as shown in FIG. 5. To this end, it uses not only the classification results but also the navigation data, the latter being used to gather the site of the macroscopic tissue region 15 at which the microscopic tissue section 16 underlying the respective classification data is situated in the macroscopic tissue region 15. The combination device 37 then uses the classification data and the navigation data to create the combination image 43, in which image regions 44 representing the individual classification results are arranged with respect to one another in the relative positioning which corresponds to the relative positioning of the microscopic tissue sections 16 depicted in the histological images. The image regions 44 representing classification results are in this case combined like a mosaic to form the classification image 43. The area taken up in the classification image 43 by the image regions 44 representing the individual classification results then represents the area of the tumor and the edge of this area taken up in the classification image 43 represents the boundary of the tumor. Accordingly, the profile of the edge of the area taken up in the classification image 43 represents the profile of the boundary between tumor tissue and healthy tissue in a tissue region 15 with a tumor 23.

In the present exemplary embodiment, the image regions 44 representing the classification results in the classification image 43 adjoin one another, as depicted in FIG. 5. However, the distance between the image regions 44 representing the classification results in the classification image 43 may also differ from what is depicted in FIG. 5. Thus, the image regions 44 representing the classification results in the classification image 43 may also overlap one another or be arranged at a distance from one another. In this case, the distances of the image regions 44 representing the classification results in the classification image 43 from one another correspond to the distances between the microscopic tissue sections 16 that form the basis of the histological images. If these tissue sections 16 overlap, there is also overlap between the image regions 44 representing the classification results in the classification image 43. By contrast, if there are gaps between some or all microscopic tissue sections 16, in which no histological image was recorded, the classification image 43 also has corresponding gaps. Interpolation can be carried out between these gaps in order to determine the profile of the edge of the area taken up by the image regions 44 representing the individual classification results in the classification image 43.

Figure 6:
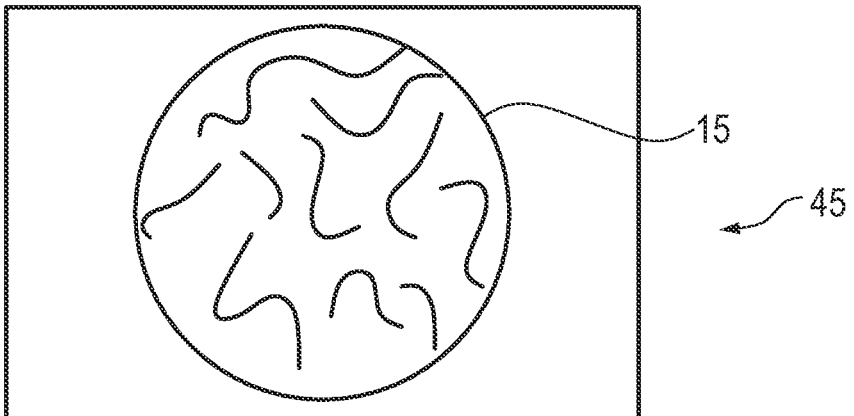
FIG. 6 shows an overview image of a tissue region.
Figure 7:
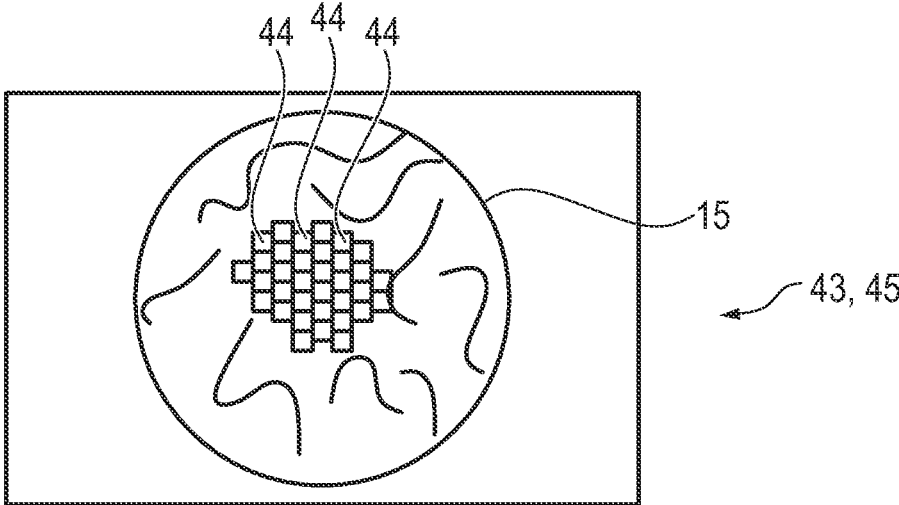
FIG. 7 shows a superposition of the classification image on the overview image.

The classification image 43 can serve as a superposition image which is overlaid on an overview image 45 (FIG. 6) of the macroscopic tissue region 15 obtained by the surgical microscope 1 (FIG. 7). Classification results representing healthy tissue can then be represented, e.g., as colorless image regions 44 in the classification image 43 while classification results representing tumor tissue can be represented as colored image regions 44. If the classification image 43 is then overlaid on the overview image 45 with a given degree of transparency, then a labeling of the tumor in the overview image 45 is obtained, from which it is possible to identify the position and extent thereof in the macroscopic tissue region 15 represented by the overview image 45 and the boundary between tumor tissue and healthy tissue. The navigation data and/or an image registration can be used to overlay the classification image 43 on the overview image with the correct position, orientation and scaling. Alternatively, there is also the option of coloring those image regions 44 of the classification image 43 that correspond to microscopic tissue section 16 with healthy tissue, in order to highlight the healthy tissue regions in the superposition. However, it is also possible to color the image regions 44 of the classification image 43 representing tumor tissue in a first color and to color the image regions 44 of the classification image 43 representing healthy tissue in a second color that differs from the first, for instance image regions 44 of the classification image 43 representing tumor tissue in red and image regions 44 of the classification image 43 representing healthy tissue in green. In the surgical microscope 1, the superposition can be implemented with the aid of the beam splitter prism 135 and the display 137, which together serve as a superposition apparatus. However, there also is the option of carrying out the superposition electronically and displaying the result of the electronic superposition on a monitor. With the aid of the superposition, it is possible to provide a treating surgeon with accurate information in respect of the location of the tumor 23, the extent of the latter and its boundary to healthy tissue. The surgeon can then use this information during the treatment, for example in order to precisely irradiate the tumor 23 or to carry out a precise resection of tumor tissue.

In the present exemplary embodiment, the classification image 43 can find use in the targeted irradiation of those sections of the macroscopic tissue region 15 that represent tumor tissue by way of the therapeutic radiation of the irradiation light source 25. Aligning the irradiation light source 25 by means of the positioning device 27 can be implemented either manually by the surgeon on the basis of the overview image 45 on which the classification image 43 has been overlaid, or by robot, with the navigation data then being used for positioning and/or aligning the beam of the irradiation light source 25.

In an alternative configuration of the disclosure, there is the option of implementing the distinction between tumor tissue and healthy tissue purely on the basis of an image obtained by the surgical microscope 1 or any other suitable medical imaging apparatus. By way of example, should the overview image 45 represent the fluorescence intensity of the macroscopic tissue region 15, tumor tissue-representing tissue sections 117 of the macroscopic tissue region 15 can be identified on the basis of the intensity of the fluorescence radiation. Instead of identifying tumor tissue on the basis of the fluorescence intensity, there also is the option of identifying tumor regions on the basis of the spectral reflection of the tissue or on the basis of the decay behavior of fluorescence radiation. Following the identification of the tumor tissue-representing tissue sections 117 of the macroscopic tissue region 15, irradiation is then implemented in targeted fashion in those tissue sections 117 of the macroscopic tissue region 15 which were identified as tumor tissue. As described above, identification can be implemented with the aid of an artificial neural network.

Figure 8:
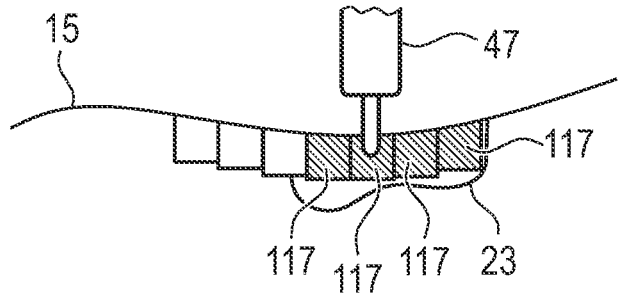
FIG. 8 shows the irradiation of a tumor with the aid of an applicator.

Instead of the irradiation light source 25 from FIG. 1, an applicator 47 can also be used to irradiate the tumor with therapeutic radiation, said applicator being brought to the tumor tissue or, as depicted in FIG. 8, inserted into the tumor tissue in order to irradiate the latter locally with therapeutic radiation. By way of example, one of the applicators for intraoperative radiotherapy as described in DE 10 2018 120 750 B3, DE 10 2008 030 590 A1, EP 2 335 778 A1 and WO 01/58346 A1 may be used as applicator 47. In this case, the applicator 47 is brought to the tumor 23 or inserted into the tumor 23 by robot on the basis of the classification image 43 or on the basis of the information, obtained with the aid of the overview image, about the position of the tumor in the macroscopic tissue region 15, with navigation data also being used. By way of example, a robotic arm can find use to this end.

The present disclosure has been described in detail on the basis of exemplary embodiments for explanatory purposes. However, a person skilled in the art recognizes that there can be deviations from the exemplary embodiments within the scope of the present disclosure. Therefore, the present disclosure is not intended to be limited by the exemplary embodiments but rather only by the appended claims.

LIST OF REFERENCE SIGNS

1 Surgical microscope
3 Endomicroscope
5 Computer
9 Tube
11 Input end
13 Output end
15 Macroscopic tissue region
16 Microscopic tissue section
17 Scanning device
19 Sensor
23 Tumor
25 Irradiation light source
27 Galvanometer scanner
29 Data processing system
31 Classification device

33 Interface
35 Interface
37 Combination device
39 Selection device
41 Marker
43 Classification image
44 Image region
45 Overview image
47 Applicator
103 Camera
105 Objective
107 Divergent beam
109 Beam
109A,B Stereoscopic partial beam path
111 Magnification changer
113A,B Interface arrangement
115A,B Beam splitter prism
117 Tissue section
119 Camera adapter
123 Image sensor
127 Binocular tube
129A,B Tube objective
131A,B Intermediate image plane
133A,B Prism
135A,B Eyepiece lens
137 Display
139 Optical unit
141 White light source
143 Deflection mirror
145 Illumination optical unit

The invention claimed is:

1. A medical optical system comprising:

an endomicroscope for recording histological images representing each of a plurality of microscopic tissue sections of a macroscopic tissue region, the macroscopic tissue region comprising a tumor, wherein each histological image has associated navigation data representing a position and an orientation of the endomicroscope used to capture the histological image;

a classification device that processes, using a neural network, the microscopic tissue sections represented in the histological images, to classify each of the microscopic tissue sections as a tissue section representing the tumor or a tissue section representing healthy tissue and for outputting a classification result for each classified microscopic tissue section, wherein the neural network is:

trained using a plurality of training samples, each particular training sample of the plurality of training samples representing a training tissue section representing a tumor or a training tissue section representing healthy tissue, and associated with a corresponding assigned classification indicating whether the training tissue section represents healthy tissue or tumor tissue; and trained to predict, for each particular training sample of the plurality of training samples, the corresponding assigned classification based on of the training tissue section represented by the respective training sample; and a combination device which generates a macroscopic classification image by combining the classification results and the navigation data indicating a spatial position of each microscopic tissue section within the macroscopic tissue region, the macroscopic classification image composed of a plurality of sections, each section comprising an indication of whether a corresponding microscopic tissue section corresponds to the tumor or the healthy tissue, and wherein spatial positioning of the microscopic tissue sections in the macroscopic classification image corresponds to relative positions of the microscopic tissue sections in the macroscopic tissue region;

optical observation equipment for producing an overview image of the macroscopic tissue region; and an overlay apparatus configured to overlay the macroscopic classification image on the overview image, wherein the overlay apparatus uses the navigation data to register the macroscopic classification image with the overview image to ensure spatial accuracy of the overlay of the microscopic classification image on the overview image.

2. The medical optical system as claimed in claim 1, wherein the combination device is configured to derive a macroscopic profile of the tumor based on the classification results.

3. The medical optical system as claimed in claim 1, wherein the classification device is configured to undertake the classifying of each microscopic tissue section based on also at least one of the following alternatives:

a decay behavior of fluorescence radiation emitted by the microscopic tissue section;

an intensity of fluorescence radiation emitted by the microscopic tissue section; or a spectral reflection property of the microscopic tissue section.

4. The medical optical system as claimed in claim 1, wherein the classification device is configured to classify each microscopic tissue section into a number of classes, of which one class represents healthy tissue and the remaining classes represent different types of tumor tissue.

5. The medical optical system as claimed in claim 1, wherein the classification device is configured to also use data from images obtained by the optical observation equipment for classifying microscopic tissue sections.

6. The medical optical system as claimed in claim 1, further comprising a treatment system for a local treatment of tissue and a positioning device for positioning the treatment system based on the navigation data such that the macroscopic tissue region is treated, the positioning device being designed to undertake the positioning based on the macroscopic classification image.

7. The medical optical system as claimed in claim 6, wherein the treatment system comprises an irradiation system for directed irradiation of the macroscopic tissue region, and the positioning device is designed to align the irradiation system with the macroscopic tissue region based on the macroscopic classification image and the navigation data for purposes of positioning said irradiation system.

8. The medical optical system as claimed in claim 6, wherein the treatment system comprises an applicator for a local application of therapeutic radiation at or in the macroscopic tissue region, and the positioning device is designed to guide the applicator to the macroscopic tissue region by means of a robot, the guidance being implemented based on the macroscopic classification image and the navigation data.

9. The medical optical system as claimed in claim 1, further comprising a scanning device for scanning the macroscopic tissue region with the endomicroscope for purposes of obtaining the histological images for a plurality of microscopic tissue sections of the macroscopic tissue region.

10. The medical optical system as claimed in claim 1, further comprising a navigation system configured to gather the navigation data.

11. A data processing system comprising:

a receiving interface for receiving histological images representing a corresponding morphology of each of a plurality of microscopic tissue sections of a macroscopic tissue region, the macroscopic tissue region comprising a tumor, wherein each histological image has associated navigation data representing a position and an orientation of an endomicroscope used to capture the histological image;

a classification device that processes, using a neural network, the microscopic tissue sections represented in the histological images, to classify each of the microscopic tissue sections represented in the histological images, as a tissue section representing the tumor or a tissue section representing healthy tissue in each case, and for outputting a classification result for each classified microscopic tissue section, wherein the neural network is:

trained using a plurality of training samples, each particular training sample of the plurality of training samples representing a training tissue section representing a tumor or a training tissue section representing healthy tissue, and associated with a corresponding assigned classification indicating whether the training tissue section represents healthy tissue or tumor tissue; and trained to predict, for each particular training sample of the plurality of training samples, the corresponding assigned classification based on the morphology of the training tissue section represented by the respective training sample; and a combination device which generates a macroscopic classification image by combining the classification results and the navigation data indicating a spatial position of each microscopic tissue section within the macroscopic tissue region, the macroscopic classification image composed of a plurality of sections, each section comprising an indication of whether a corresponding microscopic tissue section corresponds to the tumor or the healthy tissue, and wherein spatial positioning of the microscopic tissue sections in the macroscopic classification image corresponds to relative positions of the microscopic tissue sections in the macroscopic tissue region;

optical observation equipment for producing an overview image of the macroscopic tissue region; and an overlay apparatus configured to overlay the macroscopic classification image on the overview image, wherein the overlay apparatus uses the navigation data to register the macroscopic classification image with the overview image to ensure spatial accuracy of the overlay of the microscopic classification image on the overview image.

12. A non-volatile computer-readable storage medium with instructions stored thereon, wherein said instructions, when executed on a computer, cause the computer to:

receive histological images representing a corresponding morphology of each of a plurality of microscopic tissue sections of a macroscopic tissue region, the macroscopic tissue region comprising a tumor, wherein each histological image has associated navigation data representing a position and an orientation of an endomicroscope used to capture the histological image;

process, using a neural network, using a neural network, the microscopic tissue sections represented in the histological images, to classify each of the microscopic tissue sections represented in the histological images, as a tissue section representing the tumor or a tissue section representing healthy tissue in each case, and for outputting a classification result for each classified microscopic tissue section, wherein the neural network is, wherein the neural network is:

trained using a plurality of training samples, each particular training sample of the plurality of training samples representing a training tissue section representing a tumor or a training tissue section representing healthy tissue, and associated with a corresponding assigned classification indicating whether the morphology of the training tissue section represents healthy tissue or tumor tissue; and trained to predict, for each particular training sample of the plurality of training samples, the corresponding assigned classification based on the morphology of the training tissue section represented by the respective training sample; and generate a macroscopic classification image by combining the classification results and the navigation data indicating a spatial position of each microscopic tissue section within the macroscopic tissue region, the macroscopic classification image composed of a plurality of sections, each section comprising an indication of whether a corresponding microscopic tissue section corresponds to the tumor or the healthy tissue, and wherein spatial positioning of the microscopic tissue sections in the macroscopic classification image corresponds to relative positions of the microscopic tissue sections in the macroscopic tissue region;

produce an overview image of the macroscopic tissue region; and overlay the macroscopic classification image on the overview image using the navigation data to register the macroscopic classification image with the overview image to ensure spatial accuracy of the overlay of the microscopic classification image on the overview image.

13. A medical optical system comprising:

an endomicroscope for recording histological images representing a corresponding morphology of each of a plurality of microscopic tissue sections of a macroscopic tissue region, the macroscopic tissue region comprising a tumor;

a classification device that processes, using a neural network, the microscopic tissue sections represented in the histological images, to classify each of the microscopic tissue sections as a tissue section representing the tumor or a tissue section representing healthy tissue, and for outputting a classification result for each classified microscopic tissue section, wherein the neural network is:

trained using a plurality of training samples, each particular training sample of the plurality of training samples representing a training tissue section representing a tumor or a training tissue section representing healthy tissue, and associated with a corresponding assigned classification indicating whether the training tissue section represents healthy tissue or tumor tissue; and trained to predict, for each particular training sample of the plurality of training samples, the corresponding assigned classification based on the morphology of the training tissue section represented by the respective training sample; and a navigation system for gathering navigation data representing a site of the macroscopic tissue region at which the microscopic tissue section underlying respective classification data is situated, the navigation data representing a position and an orientation of the endomicroscope used to capture each histological image; and a combination device which generates a macroscopic classification image by combining the classification results and the navigation data indicating a spatial position of each microscopic tissue section within the macroscopic tissue region, the macroscopic classification image composed of a plurality of sections, each section comprising an indication of whether a corresponding microscopic tissue section corresponds to the tumor or the healthy tissue, and wherein spatial positioning of the microscopic tissue sections in the macroscopic classification image corresponds to relative positions of the microscopic tissue sections in the macroscopic tissue region;

optical observation equipment for producing an overview image of the macroscopic tissue region; and an overlay apparatus configured to overlay the macroscopic classification image on the overview image using the navigation data to register the macroscopic classification image with the overview image to ensure spatial accuracy of the overlay of the microscopic classification image on the overview image.

14. A medical optical system as claimed in claim 13, wherein, in the macroscopic classification image, regions representing individual classification results are arranged with respect to one another in relative positioning which corresponds to the relative positioning of the microscopic tissue sections by use of the navigation data.

15. A medical optical system as claimed in claim 13, wherein a spatial resolution with which a tissue section is imaged in a histological image is no greater than 20 μm.

16. A medical optical system comprising:

an endomicroscope for recording histological images representing a corresponding decay of fluorescence radiation emitted by each of a plurality of microscopic tissue sections of a macroscopic tissue region, the macroscopic tissue region comprising a tumor, wherein each histological image has associated navigation data representing a position and an orientation of the endomicroscope used to capture the histological image;

a classification device that processes, using a neural network, the microscopic tissue sections represented in the histological images to classify each of the microscopic tissue sections as a tissue section representing the tumor or a tissue section representing healthy tissue based on the corresponding decay of fluorescence radiation emitted by the respective microscopic tissue section, and for outputting a classification result for each classified microscopic tissue section, wherein the neural network is:

trained using a plurality of training samples, each particular training sample of the plurality of training samples representing a training decay of fluorescence radiation emitted by a training tissue section and associated with a corresponding assigned classification indicating whether the training decay of fluorescence radiation of the training tissue section represents healthy tissue or tumor tissue; and trained to predict, for each particular training sample of the plurality of training samples, the corresponding assigned classification based on the training decay of fluorescence radiation;

a combination device which generates a macroscopic classification image by combining the classification results and the navigation data indicating a spatial position of each microscopic tissue section within the macroscopic tissue region, the macroscopic classification image composed of a plurality of sections, each section comprising an indication of whether a corresponding microscopic tissue section corresponds to the tumor or the healthy tissue, and wherein spatial positioning of the microscopic tissue sections in the macroscopic classification image corresponds to relative positions of the microscopic tissue sections in the macroscopic tissue region;

optical observation equipment for producing an overview image of the macroscopic tissue region; and an overlay apparatus being configured to overlay the macroscopic classification image on the overview image, wherein the overlay apparatus uses the navigation data to register the macroscopic classification image with the overview image to ensure spatial accuracy of the overlay of the microscopic classification image on the overview image.

17. A medical optical system comprising:

an endomicroscope for recording histological images representing each of a plurality of microscopic tissue sections of a macroscopic tissue region, the macroscopic tissue region comprising a tumor, wherein each histological image has associated navigation data representing a position and an orientation of the endomicroscope used to capture the histological image;

optical observation equipment for producing a fluorescence image and an overview image corresponding to the macroscopic tissue region;

a classification device that processes, using a neural network, the microscopic tissue sections represented in the histological images and the fluorescence image, to classify each of the microscopic tissue sections as a tissue section representing the tumor or a tissue section representing healthy tissue and for outputting a classification result for each classified microscopic tissue section, wherein the neural network is:

trained using a plurality of training samples, each particular training sample of the plurality of training samples representing a training tissue section representing a tumor or a training tissue section representing healthy tissue, and associated with a corresponding fluorescence image and a corresponding assigned classification indicating whether the training tissue section represents healthy tissue or tumor tissue; and trained to predict, for each particular training sample of the plurality of training samples, the corresponding assigned classification based on of the training tissue section represented by the respective training sample and the corresponding fluorescence image; and a combination device which generates a macroscopic classification image by combining the classification results each indicating whether the corresponding microscopic tissue section represents the tumor tissue or the healthy tissue, the macroscopic classification image composed of a plurality of sections, each section comprising an indication of whether a corresponding microscopic tissue section corresponds to the tumor or the healthy tissue; and an overlay apparatus configured to overlay the macroscopic classification image on the overview image, wherein the overlay apparatus uses the navigation data to register the macroscopic classification image with the overview image to ensure spatial accuracy of the overlay of the microscopic classification image on the overview image.

18. The medical optical system of claim 17, wherein the optical observation equipment comprises a surgical microscope, and wherein the overlay of microscopic classification image on the overview image is presented in an eyepiece of the surgical microscope.

* * * * *